United States Patent [19]

Nandagiri

[11] 4,263,275
[45] Apr. 21, 1981

[54] HYDROALCOHOLIC AEROSOL HAIR SPRAYS CONTAINING CORROSION INHIBITORS

[75] Inventor: Arun Nandagiri, Dover, N.J.

[73] Assignee: American Cyanamid Company, Stamford, Conn.

[21] Appl. No.: 82,260

[22] Filed: Oct. 5, 1979

Related U.S. Application Data

[63] Continuation-in-part of Ser. No. 68,247, Aug. 20, 1979, abandoned.

[51] Int. Cl.³ .................................................. A61K 7/11
[52] U.S. Cl. .......................................... 424/47; 424/70
[58] Field of Search ............................................ 424/47

[56] References Cited

U.S. PATENT DOCUMENTS 4,165,367  8/1979  Chakrabarti .................... 424/DIG. 2

4,174,295  11/1979  Bargigia et al. ..................... 424/47

FOREIGN PATENT DOCUMENTS

| 2453629 | 5/1976 | Fed. Rep. of Germany | 424/47 |
| 46-27480 | 8/1971 | Japan | 424/47 |
| 50-6538 | 3/1975 | Japan | 424/47 |
| 51-12589 | 4/1976 | Japan | 424/47 |
| 51-27740 | 8/1976 | Japan | 424/47 |
| 796319 | 6/1958 | United Kingdom | 424/47 |

*Primary Examiner*—Dale R. Ore
*Attorney, Agent, or Firm*—Charles J. Fickey

[57] ABSTRACT

A hydroalcoholic, pressurized hair spray composition containing an anticorrosive agent for reducing corrosion in tinplate aerosol cans. Such compositions contain a hydrocarbon, water, a film-forming polymeric material, an organic base neutralizer, ethanol or isopropanol and as an anticorrosion agent, a phosphate salt of a quaternary ammonium compound.

3 Claims, No Drawings

HYDROALCOHOLIC AEROSOL HAIR SPRAYS CONTAINING CORROSION INHIBITORS

This application is a continuation-in-part of our previous application Ser. No. 68,247, filed Aug. 20, 1979, now abandoned.

The present invention relates to pressurized, aerosol hair spray compositions, containing a polymeric resin to hold hair in place following combing or setting. More particularly, this invention relates to hydroalcoholic, i.e., aqueous-alcoholoc, compositions of such polymers which contain an anticorrosive agent to prevent, or reduce, corrosion in tinplate aerosol cans.

Pressurized hair sprays containing various polymeric resins suitable for holding hair in place are known. They include, for example, vinyl acetate-crotonic acid copolymers, polyvinyl pyrrolidone, vinyl pyrrolidone-vinyl acetate copolymers, copolymers of methyl vinyl ether and monoethyl- or monobutyl esters of maleic acid, and copolymers of methyl methacrylate and methacrylic acid.

Typical formulations, which are described in Nandagiri et al., U.S. Patent Application Ser. No. 844,241, filed Oct. 21, 1977, now U.S. Pat. No. 4,164,562, include a neutralizing agent, such as aminomethylpropanol, triethanolamine, dimethyl stearamine, and the like; a carrier, such as denatured alcohol, or isopropanol; a perfume; a co-solvent and a propellant. The neutralizer is optional and is needed only when the film-forming polymer contains carboxyl groups. Recent changes in the type of propellants used, from fluorocarbon to hydrocarbon, have made it necessary to include a flame retardant to suppress the flammability of these hydrocarbon-propelled formulas. Such compositions, containing water as a flame retardant, are disclosed in the aforementioned application pending with the U.S. Patent Office. While these formulations are effective in reducing the flammability of the hair spray product, they create a serious corrosion problem with tinplate aerosol cans. This is due to the electrical conductivity of the hydroalcoholic concentrate. As the water content in the formulation is increased, the electrical conductivity will also increase, causing the formulation to be more corrosive. The pH of the concentrate is also an important factor affecting the corrosion rate. As a general rule, the acidic formulas are more corrosive than neutral or alkaline formulations, although corrosion is a problem even with them. The actual rate at which a given metal corrodes at a particular pH depends on various factors, such as oxygen concentration, polarization, chloride content, water content, and the like. Formulations which are acidic, such as those based on copolymers of methyl vinyl ether and monoethyl- or monobutyl esters of maleic acid and which have high water content, have the greatest potential for can corrosion, resulting in very short shelf-life.

The present invention provides a hair spray composition containing a phosphate salt of quaternary ammonium compound, which greatly reduces the corrosion potential of these hydroalcoholic formulations, especially acidic formulations.

The general formula of the quaternary ammonium compound is represented as follows:

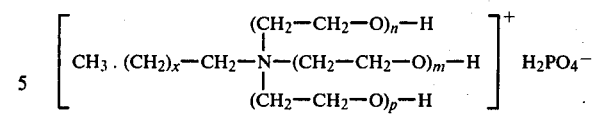

wherein x is an integer from about 12 to 18 and m, n, and p are integers, the sum of which total from about 3 to 12.

Quaternary ammonium compounds, representative of the above class, are commercially available, and one such compound, Dehyquart SP (Henkel, Inc., Hoboken, New Jersey), has the following formula:

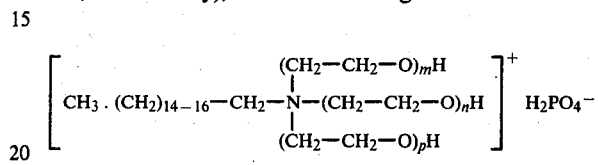

where $m+n+p$ has an average value of 10.

It has been found that the addition of from about 0.1 to 3% of the quaternary compound to the hydroalcoholic formulations greatly reduces the corrosion of tinplate aerosol cans. The concentration is critical, since below 0.1% the corrosion inhibition is not readily observed and above 3% the formulation would have negative tactile properties on hair. In addition to having corrosion inhibiting activity, the quaternary compounds act as a plasticizer and give the hair a soft feel. Since they are quaternary ammonium compounds, they have excellent antistatic and emulsifying properties and have been recommended for use in cosmetics, especially in hair conditioning preparations such as home permanents, hair rinses, hair-setting sprays and hair lotions.

The following examples are given by way of illustration only and are not intended as limitations of this invention, especially its use as a corrosion inhibitor in formulations other than in hair sprays.

EXAMPLE 1

An aerosol hair spray is prepared by mixing the following ingredients:

| Ingredients | % W/W |
|---|---|
| Ethanol Anhydrous | 44.18 |
| 2-Amino-2-methyl-1-propanol | 0.17 |
| Gantrez ES 225* (as is) | 5.00 |
| Water | 30.00 |
| Fragrance | 0.15 |
| Dehyquart SP (50% solution) | 0.50 |
| Hydrocarbon A-31 (Isobutane) | 20.00 |
| | 100.00 |

EXAMPLE 2

| Ingredients | % W/W |
|---|---|
| Ethanol Anhydrous | 44.68 |
| 2-Amino-2-methyl-1-propanol | 0.17 |
| Gantrez ES 225* (as is) | 5.00 |
| Water | 30.00 |
| Fragrance | 0.15 |
| Hydrocarbon A-31 (Isobutane) | 20.00 |
| | 100.00 |

*Copolymer of monoethyl ester of maleic acid and methyl vinyl ether

EXAMPLE 3

| Ingredients | % W/W |
|---|---|
| Ethanol Anhydrous | 57.68 |
| 2-Amino-2-methyl-1-propanol | 0.17 |
| Gantrez ES 225* (as is) | 5.00 |
| Methylene Chloride | 12.00 |
| Fragrance | 0.15 |
| Hydrocarbon A-31 (Isobutane) | 25.00 |
|  | 100.00 |

Accelerated storage testing was done at 45° C. with tinplate aerosol cans with all three compositions shown above. It was found that the composition shown in Example 2 (no quaternary compound) deteriorated rapidly with can perforations being observed within 12–16 weeks. In contrast, the composition shown in Example 1, which contained 0.5% Dehyquart SP, and composition shown in Example 3, which did not contain any water, did not show any changes to the product or the container.

EXAMPLE 4

| Ingredients | % W/W |
|---|---|
| Ethanol Anhydrous | 44.35 |
| PVP/VA** E-735 (as is) | 5.00 |
| Water | 30.00 |
| Fragrance | 0.15 |
| Dehyquart SP (50% Solution) | 0.50 |
| Hydrocarbon A-31 (Isobutane) | 20.00 |
|  | 100.00 |

*Copolymer of monoethyl ester of maleic acid and methyl vinyl ether
**Copolymer of polyvinylpyrrolidone and vinyl acetate

EXAMPLE 5

| Ingredients | % W/W |
|---|---|
| Ethanol Anhydrous | 44.85 |
| PVP/VA* E-735 (as is) | 5.00 |
| Water | 30.00 |
| Fragrance | 0.15 |
| Hydrocarbon A-31 (Isobutane) | 20.00 |
|  | 100.00 |

EXAMPLE 6

| Ingredients | % W/W |
|---|---|
| Ethanol Anhydrous | 62.85 |
| PVP/VA* E-735 (as is) | 5.00 |
| Methylene Chloride | 12.00 |
| Fragrance | 0.15 |
| Hydrocarbon A-31 (Isobutane) | 20.00 |
|  | 100.00 |

*Copolymer of polyvinylpyrrolidone and vinyl acetate

Accelerated storage testing results of composition shown in Example 5 were similar to those observed with composition shown in Example 2, with can failures being observed in 12–16 weeks. Results of compositions shown as Examples in 4 and 6 were similar to those shown in Examples 1 and 3, with minimum changes being observed in product or container stability.

EXAMPLE 7

| Ingredients | % W/W |
|---|---|
| Ethanol Anhydrous | 66.18 |
| 2-Amino-2-methyl-1-propanol | 0.17 |
| Gantrez ES-225 | 5.00 |
| Water | 8.00 |
| Fragrance | 0.15 |
| Dehyquart SP (50% solution) | 0.50 |
| Hydrocarbon A-31 (Isobutane) | 20.00 |
|  | 100.00 |

EXAMPLE 8

| Ingredients | % W/W |
|---|---|
| Ethanol Anhydrous | 66.68 |
| 2-Amino-2-methyl-1-propanol | 0.17 |
| Gantrez ES-225 | 5.00 |
| Water | 8.00 |
| Fragrance | 0.15 |
| Hydrocarbon A-31 (Isobutane) | 20.00 |
|  | 100.00 |

EXAMPLE 9

| Ingredients | % W/W |
|---|---|
| Ethanol Anhydrous | 62.68 |
| 2-Amino-2-methyl-1-propanol | 0.17 |
| Gantrez ES-225 | 5.00 |
| Methylene Chloride | 12.00 |
| Fragrance | 0.15 |
| Hydrocarbon A-31 | 20.00 |
|  | 100.00 |

Accelerated storage testing results of composition shown in Examples 7 and 9 were similar with minimum changes being observed in product or container stability. However, composition shown in Example 8 showed surface detinning with single-lined tinplate cans when stored under the same conditions.

EXAMPLE NO. 10

|  | A | B |
|---|---|---|
| Ethanol Anhydrous | 63.94 | 46.94 |
| 2-Amino-2-methyl-1-propanol | 0.41 | 0.41 |
| *Amphomer | 2.50 | 2.50 |
| Water | 8.00 | 25.00 |
| Fragrance | 0.15 | 0.15 |
| Hydrocarbon A-31 (Isobutane) | 25.00 | 25.00 |
|  | 100.00 | 100.00 |

EXAMPLE NO. 11

|  | A | B |
|---|---|---|
| Ethanol Anhydrous | 63.44 | 46.44 |
| 2-Amino-2-methyl-1-propanol | 0.41 | 0.41 |
| *Amphomer | 2.50 | 2.50 |
| Water | 8.00 | 25.00 |
| Fragrance | 0.15 | 0.15 |
| Dehyquart SP (50% solution) | 0.50 | 0.50 |
| Hydrocarbon A-31 (Isobutane) | 25.00 | 25.00 |
|  | 100.00 | 100.00 |

EXAMPLE NO. 12

| | |
|---|---|
| Ethanol Anhydrous | 59.94 |
| 2-Amino-2-methyl-1-propanol | 0.41 |
| *Amphomer | 2.50 |
| Methylene Chloride | 12.00 |
| Fragrance | 0.15 |
| Hydrocarbon A-31 (Isobutane) | 25.00 |
| | 100.00 |

*Octylacrylamide/acrylates/Butylaminoethylmethacrylate polymer

Accelerated storage testing results did not show a substantial difference in can corrosion between Examples No. 10A, B, 11A, B and 12. This is because these formulations are basic pH. However when the chloride content in the deionized water was increased above 10 ppm, formulations contaning the Dehyquart SP (Example No. 11A and B) were observed to be as good as the anhydrous formula shown in Example No. 12 while Example No. 10A and B showed surface detinning.

We claim:

1. A hair spray composition comprising (a) about 60 to 90 percent by weight of a liquid concentrate phase, and (b) about 10 to 40 percent by weight of a propellant phase selected from the group consisting of propane, n-butane, isobutane, or mixtures thereof; said liquid concentrate phase, based on the total weight of (a) and (b), consists of from about 1 to 7% of a film-forming polymeric material; from 2 to 40 percent by weight water; from 0.05 to 0.6 weight percent of an organic base neutralizer; 0.1 to 3 percent by weight of a phosphate salt of a quaternary ammonium compound represented by the formula:

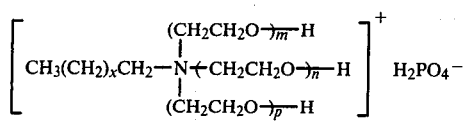

wherein x is an integer from about 12 to 18 and m, n, and p are integers the sum of which total from about 3 to 12 as a corrosion inhibitor; and sufficient ethanol or isopropanol, or mixture thereof, to total 100 percent.

2. A composition according to claim 1 wherein x is an integer from 14–16 and $m+n+p$ has an average of about 10.

3. A composition according to claim 1 wherein said film-forming copolymeric material is a vinyl acetate-crotonic acid copolymer, a polyvinylpyrrolidone copolymer, a vinylpyrrolidone-vinyl acetate copolymer, copolymers of methylvinyl ether and monoethyl ester of maleic acid, or monobutyl ester of maleic acid, or a copolymer of methyl methacrylate and methacrylic acid.

* * * * *